United States Patent
Oswald et al.

(10) Patent No.: US 6,923,649 B2
(45) Date of Patent: Aug. 2, 2005

(54) ARTIFICIAL TOOTH AND A PROCESS FOR MAKING AN ARTIFICIAL TOOTH

(75) Inventors: Walter Oswald, Frastanz (AT); Eduard Tenschert, Nenzing-Beschling (AT)

(73) Assignee: Ivoclar Vivadent AG, Schaan (LI)

( * ) Notice: Subject to any disclaimer, the term of this patent is extended or adjusted under 35 U.S.C. 154(b) by 142 days.

(21) Appl. No.: 10/177,050

(22) Filed: Jun. 20, 2002

(65) Prior Publication Data

US 2002/0187457 A1 Dec. 12, 2002

Related U.S. Application Data

(60) Provisional application No. 60/308,680, filed on Jul. 30, 2001.

(30) Foreign Application Priority Data

Jun. 7, 2001 (DE) .......................... 101 27 728

(51) Int. Cl.[7] .............................. A61C 13/08
(52) U.S. Cl. ...................... 433/212.1; 433/223; 264/19
(58) Field of Search .............................. 433/223, 222.1, 433/212.1, 202.1; 264/19, 20; 249/54

(56) References Cited

U.S. PATENT DOCUMENTS 5,775,913 A * 7/1998 Updyke et al. .............. 433/223
6,488,503 B1 * 12/2002 Lichkus et al. .......... 433/202.1

FOREIGN PATENT DOCUMENTS

DE 36 10 683 A1 10/1987

* cited by examiner

*Primary Examiner*—Melba Bumgarner
(74) *Attorney, Agent, or Firm*—John C. Thompson; Alan S. Korman

(57) ABSTRACT

An artificial tooth is provided that includes a cutting mass brought into hardened condition by light polymerization, a tooth bone mass brought into hardened condition by light polymerization, and a base mass. Those masses bordering one another are intensively interconnected with one another. The process for producing an artificial tooth includes subjecting the cutting mass disposed in a mold to light polymerization, subsequently disposing the tooth bone mass on the first mass while the cutting mass is still disposed in the mold, and subjecting the tooth bone mass to light polymerization with light passed through the mold and the cutting mass disposed in the mold.

9 Claims, 1 Drawing Sheet

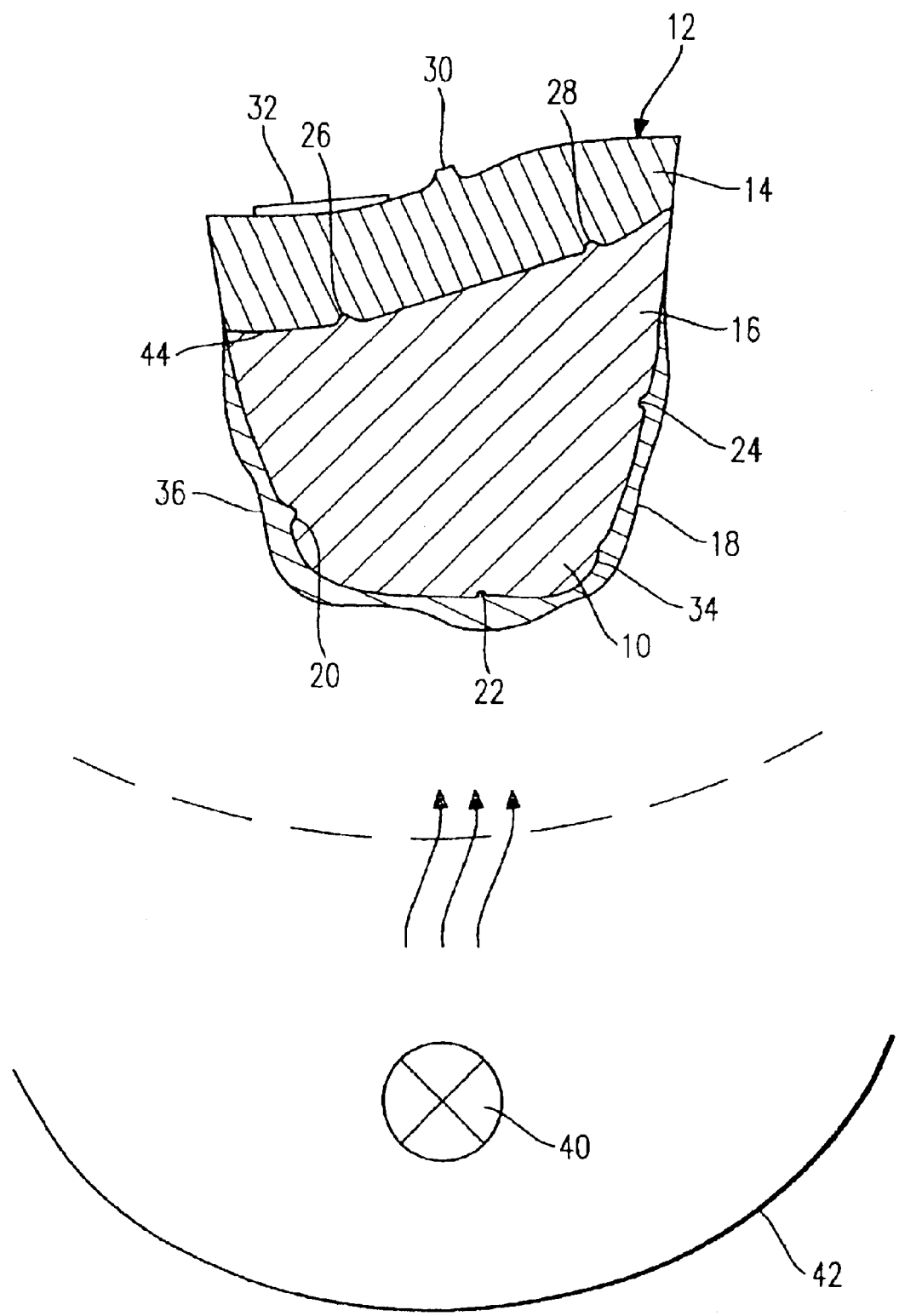

ARTIFICIAL TOOTH AND A PROCESS FOR MAKING AN ARTIFICIAL TOOTH

CROSS-REFERENCE TO RELATED APPLICATIONS

This application claims foreign priority benefits under 35 U.S.C. §119(a)–(d) from German patent application ser. no. 101 27 728.8 filed Jun. 7, 2001. In addition, this application claims the benefit under 35 U.S.C. §119(e) of U.S. provisional patent application Ser. No. 60/308,680 filed Jul. 30, 2001.

This application claims the benefit of U.S. Provisional Application No. 60/308,680, filed Jul. 30, 2001.

BACKGROUND OF THE INVENTION

The present invention relates to an artificial tooth and a process for making an artificial tooth.

It is known to use polymerizable material in the dental practice which is hardenable into its finished condition by light or thermal polymerization thereof as well as, in some instances, by the application of pressure thereto. In order to undertake a light hardening process, the light must have an undisturbed access to the mass to be polymerized, whereby it has become conventional to provide transparent molds for the prostheses themselves. A solution of this type is disclosed in DE-OS 36 10 683. In this disclosed tooth prosthesis, an especially polymerizable mass is used for the production of a form or mold piece which remains white in color and which is comprised of, among other components, urethane oligomers. A model for the prosthesis is produced in connection with the manufacture of such a prosthesis with the model having a transparent mold overpiece. A disadvantage of this approach is, however, the substantial effort required for the separate production of a soft elastic mold component which is to be combined with a completely hardened artificial or plastic material.

It has further already been suggested to produce an artificial tooth comprised entirely of light polymerizable material. Such artificial teeth must be especially wear-resistant, so that the surface quality of the teeth is measured against stringent standards. This process has not yet found any acceptance in practice.

Artificial teeth are much more typically comprised of a ceramic mass. A tooth produced in this manner is relatively hard and exhibits a good surface quality. The tooth is also wear-resistant and is sufficient, when produced with corresponding care and the use of corresponding forming techniques, to satisfy today's aesthetic demands. A certain disadvantage of teeth produced of ceramic sinter masses is that these teeth have a surface which is harder than the natural tooth bloom.

Thus, those surfaces of teeth in the mouth of the patient which are in opposition to the artificial tooth are placed under relatively strong demands. On the other hand, artificial or composite material teeth have the advantage that they are, at least, somewhat softer than natural teeth. Artificial teeth, i.e. teeth of polymeric material, have, in contrast to ceramic teeth, certain advantages, whereby a reduced wearing away of the oppositional surfaces relative to the inserted artificial teeth is one of these advantages.

Plastic or artificial material is, on the other hand, less resistant to pressure and is correspondingly more susceptible to wear than ceramic so that, in the production of such artificial teeth, care must be paid to ensure that the potentially achievable material properties are optimized.

In order to produce an artificial tooth which is particularly resistant to wear and that is hard, selected plastic or artificial material is used such as, typically, a methyl methacrylate derivative. Evaluations have shown that the manner of the polymerization, and the care exercised in performing such polymerization, is a decisive factor in determining the surface quality and the surface hardness of the artificial tooth produced by this process. In this connection, an artificial tooth is typically polymerized under comparatively high pressure at a correspondingly increased or raised temperature.

In order to meet the aesthetic demands of the present day dental practice, differing or varying layers are used—namely, a transparent layer, which is intended to simulate the natural tooth bloom, and an opaque layer, which is intended to simulate the tooth bone. These layers are each produced under a corresponding pressure and corresponding temperature in connection with their polymerization and each forms a respective shell-shaped body. In connection with this approach, care must be taken that a secure connection between the layers is ensured so that the artificial tooth does not come apart into its individual components.

This process is, however, one which requires substantial effort in that a multitude of molds and/or mold inserts must be used which must be regularly cooled in an alternating manner and must also be regularly heated or warmed in an alternating manner. A further problem lies in the fact that the artificial material is subjected to a multiple—for example, four-fold—heating up beyond its melting point and is then subjected to an intensive cooling off, all of which leads to a deterioration or negative impact on its material properties. On the other hand, it is practically not possible to heat and put under pressure only that sole layer which is to be completely hardened for the reason that the layer lies in close relationship to the neighboring layer unless completely separate forms or molds are used. In spite of these disadvantages, there have been heretofore no alternative approaches for optimizing the production of artificial teeth.

OBJECTS AND SUMMARY OF THE INVENTION

The present invention offers a solution to the challenge of providing an artificial tooth whose production can be accomplished by a simpler and more rapid production process while nonetheless having improved surface quality precisely in the cutting region of the artificial tooth.

The process of the present invention for producing an artificial tooth surprisingly permits the production of such a tooth with at least a homogeneous or uniform quality. Instead of the tooth undergoing a pressure and, in particular, a temperature cycle during its production, a multiple light polymerization process is performed and, indeed, is performed by passage of the polymerizing light through mold pieces which, in accordance with the present invention, permit the passage of such light therethrough. The artificial tooth of the present invention is characterized throughout in that it is comprised of layers and the layers are intensively connected with one another. The artificial tooth is formed completely of light polymerizable material, whereby the cutting mass is more transparent than the tooth bone mass. This produces several particular effects which are exploited optimally in connection with the present invention.

Firstly, the cutting mass is more transparent than the tooth bone mass so that, during the light irradiation of the later-applied tooth bone mass, the light passage capability of the light through the cutting mass is particularly good. Those masses which are more difficult for light to reach can thus be irradiated in an improved manner, which thus permits a compensation to be realized so that neither the light output nor the length of time of irradiation for effecting the hardening of the tooth bone mass need be especially high.

On the other hand, the cutting mass is particularly intensively irradiated with light beams precisely on its surfaces adjacent the mold. This contributes to ensuring that these surfaces attain a particular hardness and display an improved surface quality.

Moreover, the light polymerization process provides the possibility to accommodate or tailor the intensity of the connection between the individual layers or masses in accordance with the requirements at hand. Thus, an artificial tooth of the present invention can be produced which is only fully or completely polymerized after the completion of all of the light polymerization steps. The border layers or interfaces between the individual masses remain, at least initially during the performance of this process, still soft and contact-friendly, so that the intensive interconnection in accordance with the present invention is automatically produced.

It is to be understood that the manner and type of irradiation can be accommodated to a wide range of requirements. For example, in connection with one advantageous embodiment of the present invention, the irradiation for the cutting masses is short and intensive—thus, for example, accomplished with only a relatively short stand off distance from the irradiation source—and the irradiation of the tooth bone or additional masses is correspondingly less intensive and longer. Also, the frequency and the periods of irradiation can be accommodated to the requirements, whereby it is also possible to use a pulsed irradiation. In connection with the types of light to be used, any desired suitable types of irradiation can be used—that is, electromagnetic waves in those areas in which such polymerization by such irradiation is possible and, in particular, ultraviolet light.

In accordance with the present invention, it is particularly advantageous if the one after another overlying border surfaces are formed such that material injection or pouring projections remain. These projections contribute, in any event, to an interlocking and even further improved anchoring or interconnection of the layers to one another. At the same time, the misalignment or offset positions of the injection projections at these locations contribute to a separation line-free production of the cutting surfaces. The cutting masses can surround the tooth in a full-surface manner, without requiring follow-up work to achieve this result and the corresponding negative influence on the surface quality resulting from such follow-up work.

In total, the present invention offers a surprisingly good surface hardness and total quality for the artificial tooth produced in accordance with the present invention, whereby, however, the production time is drastically shortened in comparison to the heretofore conventional production processes.

The process of the present invention preferably uses building forms, which are, in accordance with an advantageous embodiment of the process of the present invention, formed to permit the passage of light therethrough. The cutting building form permits the cutting mass to be prehardened separately in the desired configuration in the mold, in that the light irradiation in accordance with the present invention is performed.

Following the light irradiation of the cutting mass, there occurs in the course of the light polymerization a certain hardness gradient, which is exploited in accordance with the present invention in that the light polymerization is ended or stopped following the passage of a predetermined period of time so that the backside of the cutting area—that is, the border surface of the cutting mass with the tooth bone mass—is not yet completely hardened, while the remainder of the cutting mass is, however, completely hardened.

In this semi-finished condition, the building form is removed and replaced by a new building form, the tooth bone building form, which permits the filling of the tooth bone mass. After the filling of the tooth bone mass, the light polymerization is resumed, whereby not only the border surface of the cutting mass relative to the tooth bone mass is brought to a complete hardened condition but also the tooth bone mass as well is polymerized to a complete hardened condition with the exception, as desired, of its backside region which, in accordance with an advantageous embodiment of the present invention, still remains to be brought into contact with a base mass. The base mass is more opaque than the tooth bone mass and, in a third step, is polymerized by a light polymerization process in a corresponding manner.

In accordance with one modification of the process of the present invention, different layers are polymerized such as, for example, a forward or front cutting area and, in connection with the tooth bone mass, a neck and back cutting area. It is to be understood that, to this extent, the color imparted to the masses which are so deployed can be accommodated to a wide range of requirements—that is, such colors can be accommodated to the desired aesthetic overall qualities.

In accordance with the present invention, it is particularly advantageous that a seamless encircling cutting area can be produced. The building forms used in connection with the present invention permit the formation of the cutting mass in an encircling manner by injection of the cutting mass into the correspondingly thin gap between the mold and the cutting mass building form. To improve the injection quality, it can be provided, in connection with this approach, that more than a single injection dose is used such as, for example, four injection doses distributed around the gap circumference.

The cutting mass thus produced has a substantially bucket-shaped body whose wall thickness is dependent upon the dimensioning of the inner surface of the mold. The mold separation follows—with further regard to the perspective of the cutting mass as a bucket—along the bucket edge so that, in any event, it is not coincidental with the outer cutting mass surface and, correspondingly, to this extent, no quality encroachments need be feared.

Also, the openings for the release passage of air during the production of the cutting mass can be configured on the portion of the surface turned toward the tooth bone mass and these release air openings require no follow-up work. Instead, these interruptions of the smooth surfaces result in an improvement of the interconnecting capability of the interlocking connections.

It is to be understood that the further transition points—that is, especially, transition points between a base mass and a tooth bone mass—can be configured in a corresponding manner. In accordance with the present invention, it is particularly advantageous if the artificial material—that is, the tooth bone mass as well as the cutting mass—is an inorganic or organic-filled light and heat hardenable monomer. In particular, different methacrylate connections are suitable for this task. The filler percent composition can preferably be in the range between 45 and 65%. The filler composition includes a monomer having a very reduced viscosity such that it is injectable via a thin needle or the like. On the other hand, in connection with a filler material of this type, the shrinkage of such material in connection with the hardening thereof is substantially small and this is especially so if glass particles or pyrogens and/or collapsed silica or silicic acid is used as the filler material. The core or kernel size should preferably be between 0.7 and 20 microns, whereby a kernel size of less than 5 microns promotes the polishing receptiveness of the cutting mass surface. Basically, organic filling materials should be considered which promote the polishing receptiveness, whereby, for example, very fine cross-linked polymers can be used.

BRIEF DESCRIPTION OF THE DRAWING

The object and advantages of the present invention will appear more clearly from the following specification in conjunction with the accompanying schematic drawing, in which:

The sole FIGURE of the drawing shows an artificial tooth produced in accordance with the present invention, the artificial tooth being shown in cross-section.

DETAILED DESCRIPTION OF THE PREFERRED EMBODIMENT

As seen in the sole FIGURE of the drawing, an artificial tooth 10 is comprised entirely of a light polymerizable material. In the embodiment illustrated, the artificial tooth is configured of three surfaces, whereby a base surface 12 extends from a base mass 14 and forms the base of the tooth. A tooth bone mass 16 is formed on the base mass 14 and the tooth bone mass 16 is covered by a cutting mass 18.

The masses exhibit, as viewed in a direction from top to bottom—that is, from the base mass toward the cutting mass—increasing transparency.

The masses are produced in a layered and sequential manner commencing with the cutting mass 18, thereafter, the tooth bone mass 16, and, finally, the base mass 14. In accordance with the production thereof by injection molding, the masses each include injection projections, whereby the cutting mass illustrated in the sole FIGURE of the drawing includes three injection projections 20, 22, and 24; the tooth bone mass includes two injection projections 26 and 28; and the base mass includes one injection projection 30. The injection projections 20, 22, 24, 26, 28, and 30 each extend respectively into the respective neighboring mass and are surrounded thereby. In this manner, the interconnection between the neighboring masses is intensified.

The base mass 14 is provided on its base surface 12 with a recognition or indicia field 32 which permits an indicia to be applied by pressing of the indicia onto the indicia field 32 during the production process or by applying a marking in a conventional manner by a corresponding pouring insert.

In the illustrated embodiment of the artificial tooth of the present invention, the tooth bone mass includes from its border surface 34 with the cutting mass 16 outward a substantially smooth or flat surface. In view of the fact that the surface 36 of the cutting mass 18 is strongly structurally accommodated and conformed to the (not illustrated) mold, there arises an uneven or non-uniform layer thickness of the cutting mass 18 on the tooth bone mass 16. This configuration permits the appearance of the artificial tooth to even more closely resemble that of a natural tooth.

There follows hereafter a description of the production of an artificial tooth in accordance with the present invention.

The mold is initially provided with a first building form, the cutting mass building form. The surface of the building form corresponds to, and shapes the configuration of, the surface of the tooth bone mass 16 along its border surface 34. Thus there is formed a seamless and surrounding gap between the mold and the cutting mass building form or forms.

This gap is then filled with the cutting mass in monomer form and, in fact, is filled via the injection projections 20, 22, and 24. Additionally, air release openings are provided in the building forms (these openings are not shown) and these openings, in any event, leave tracks in the border surface 34. As soon as the filling of the cutting mass 18, with its good flowing capabilities and not yet polymerized properties, has been completed, the light polymerization is performed and this is accomplished by irradiation of the cutting mass 18 by a light source 40.

The light irradiation passes through the light passage permitting mold, whereby it is advantageous to maintain the material thickness of the mold in as substantially uniform a manner as possible in order to promote the uniformity of the intensity of the irradiation from all sides.

Additionally, a reflector 42 is provided which promotes uniform irradiation of the cutting mass and whose diameter is considerably larger than the diameter of the artificial tooth 10 such as, for example, three times larger.

The irradiation of the cutting mass by the schematically shown light source 40 is performed for a predetermined time.

Following the period of irradiation, the cutting mass 18 is hardened but is not, however, hardened fully through. In particular, on the portion of its surface facing away from the light source, the cutting mass is still somewhat soft but not so soft that portions of the cutting mass 18 would remain hanging on the cutting mass building forms during the pulling out or removal of the cutting mass building forms.

After the removal of the cutting mass building forms, a new building form is inserted whose surface corresponds to the border surface 44 between the tooth bone mass 16 and the base mass 14. Tooth bone mass 16 is injected via the injection projections 26 and 28 into the hollow space which is formed between the separation surface 34 and the tooth bone mass building forms.

Following the filling of the building forms with the tooth bone mass, which is accomplished under the typical injection molding pressure, the partially or semi-finished artificial tooth is then subjected to another light polymerization process. The length and intensity of the irradiation can be accommodated to the strength of the material which is to be polymerized so that the light irradiation for effecting the hardening of the tooth bone mass can be selected to be a larger irradiation than the light irradiation for effecting the hardening of the cutting mass 18.

The light irradiation is accomplished, in any event, by passage of the light through the cutting mass 18. Due to the fact that the cutting mass 18 is particularly translucent and permits the unimpeded passage therethrough of light, the irradiation of the tooth bone mass 18 is only slightly dampened, or not dampened at all, by the passage of the light through the cutting mass 18. A side effect of this second light irradiation lies in the fact that the cutting mass is, particularly in the region of its border surface 34, now completely hardened through.

The light hardening of the tooth bone mass 16 is performed to an extent such that the tooth bone mass 16 is form stable without, however, its border surface 44, which borders on the base mass 14, having been brought to its complete hardness.

After the removal of the tooth bone mass building forms, a base mass building form is inserted whose surface corresponds to the base surface 12. The intermediate space which is thereby formed between the base mass building forms and the border surface 44 is then filled with the base mass, whereby an injection projection 30 is used.

Following the completion of the filling of the base mass, the light source 40 is again actuated and a through hardening of those regions of the tooth bone mass which neighbor the border surface 44 as well as the base mass 14 is undertaken.

While the light hardening somewhat warms the artificial tooth 10, this warming is not so strong as to burden or restrict the polymerization of the newly-introduced mass that is, the base mass 14 added after the hardening of the tooth bone mass 16. Thus, the individual light hardening steps are performed at a temperature substantially below the through hardening temperature of the material or mass to be polymerized and, especially, at a temperature substantially corresponding to room temperature. After the completion of these individual steps, which comprise the process of the present invention, the now-completely light polymer-ized artificial tooth 10 is removed from the mold and, thereafter, the base mass building forms are removed. Subsequently, the hardness of the artificial tooth is increased by a hot air treatment. This can be performed, for example, in an automatic manner in that the removed artificial tooth can be conveyed through a hot air station by a transport belt to completely harden the tooth. Thereafter, as required, a surface treatment such as a polishing of the surface 36 can be undertaken and also, corresponding molding techniques can be performed, if these are desired.

It is to be understood that a plurality of such artificial teeth can be produced simultaneously and can accordingly be completed with a high throughput. The finishing of such artificial teeth can also readily be made automatic. It is to be understood that the form or mold for the material which is deployed can be accommodated to the wavelength of the irradiating light. If, for example, a light irradiation is to be performed not with visible light but, rather, with UV light, then the mold material must be configured to permit passage therethrough of ultraviolet or UV light. In one modification of the present invention, the process of the present invention can also be implemented for producing cutting shells. This permits a blunted or cut-down tooth of a patient to be used as the mold, whereby it is to be understood that the term "artificial tooth" also encompasses such shells or partial teeth.

An evaluation of the artificial tooth produced in accordance with the present invention revealed that the desired finished hardness is particularly good. Also, the interconnectivity is surprisingly good. A mass difference of less than 0.08 mm was detected so that, in total, in particular with a view towards drastic reduction of the cycle time, the present invention considerably improves the production cycle time.

In a further embodiment, a building form is comprised of a material not permitting the passage of light therethrough. The use of such a building form enables a screening against light hardening at the desired positions, if necessary. After removal of the building form a complete hardening can then be achieved.

The present invention is, of course, in no way restricted to the specific disclosure of the specification and drawings, but also encompasses any modifications within the scope of the appended claims.

What is claimed is:

1. A process for producing an artificial tooth having layers built up from polymerized masses, comprising:

disposing a first cutting mass in a light passage permitting mold;

subjecting the first mass to light polymerization to effect at least partial hardening of the first mass;

subsequently disposing a second mass on the first mass while the at least partially hardened first mass is still disposed in the mold; and subsequently subjecting the second mass to light polymerization by irradiation of the second mass at least partially by light passed through the light passage permitting mold and the first mass disposed in the mold.

2. A process according to claim 1, wherein a plurality of building forms are used in association with the light passage permitting mold to form layers of an artificial tooth.

3. A process according to claim 2, wherein the building forms are comprised of a material permitting the passage of light therethrough.

4. A process according to claim 2, wherein one of the building forms for realizing an individual process step is comprised of a material which does not permit the passage of light therethrough.

5. A process according to claim 1, wherein a building form is disposed in the light passage permitting mold, a hollow space being formed between the building form and the light passage permitting mold which corresponds to the respective layer in the artificial tooth which is formed by the cutting mass, and injecting the cutting mass into the hollow space to form the respective layer.

6. A process according to claim 1, wherein the artificial tooth is subjected to complete through hardening.

7. A process according to claim 1, wherein the individual steps are performed at a temperature substantially below the through hardening temperature of the mass to be polymerized or at a temperature substantially corresponding to room temperature.

8. A process according to claim 1, wherein, following the completion of the individual production steps, the tooth is brought to complete hardness by thermal handling.

9. A process according to claim 1, further including the following steps:

subsequently disposing a third mass on the second mass while the at least partially hardened second mass is still disposed in the light passage permitting mold; and subsequently subjecting the third mass to light polymerization by irradiation of the third mass at least partially by light passed through the light passage permitting mold and the first and second masses disposed in the mold.

* * * * *